US008175076B2

(12) United States Patent
Pelzek et al.

(10) Patent No.: US 8,175,076 B2
(45) Date of Patent: May 8, 2012

(54) MEDICAL DEVICE SYNCHRONIZATION SYSTEM FOR USE IN CARDIAC AND OTHER PATIENT MONITORING

(75) Inventors: Bryon Pelzek, Chicago, IL (US); Hongxuan Zhang, Schaumburg, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 910 days.

(21) Appl. No.: 12/207,989

(22) Filed: Sep. 10, 2008

(65) Prior Publication Data

US 2009/0131762 A1    May 21, 2009

Related U.S. Application Data

(60) Provisional application No. 60/989,220, filed on Nov. 20, 2007.

(51) Int. Cl.
*H04J 3/06* (2006.01)
(52) U.S. Cl. ......................... 370/350; 370/503; 370/509
(58) Field of Classification Search .................. 370/350, 370/503, 509
See application file for complete search history.

(56) References Cited

U.S. PATENT DOCUMENTS

| | | | |
|---|---|---|---|
| 6,366,805 B1 | 4/2002 | Lutz | |
| 6,735,711 B2 * | 5/2004 | Lutz | 713/500 |
| 6,988,215 B2 * | 1/2006 | Splett et al. | 713/400 |
| 7,079,977 B2 | 7/2006 | Osorio et al. | |
| 7,187,979 B2 * | 3/2007 | Haubrich et al. | 607/60 |
| 2006/0242096 A1 * | 10/2006 | Ozaki et al. | 706/23 |
| 2007/0251835 A1 | 11/2007 | Mehta et al. | |
| 2007/0253021 A1 | 11/2007 | Mehta et al. | |
| 2007/0254593 A1 | 11/2007 | Jollota et al. | |
| 2007/0255116 A1 | 11/2007 | Mehta et al. | |
| 2007/0258395 A1 | 11/2007 | Jollota et al. | |
| 2009/0081951 A1 * | 3/2009 | Erdmann et al. | 455/41.2 |

* cited by examiner

*Primary Examiner* — Luat Phung
(74) *Attorney, Agent, or Firm* — Alexander J Burke

(57) ABSTRACT

A system provides synchronization between different medical signal (e.g., EKG and ICEG signal) acquisition and processing devices. A system synchronizes multiple different patient medical parameter processing devices, using a master clock generator. The master clock generator is adaptively programmable to provide synchronization clocks having frequencies compatible with multiple different medical devices for acquiring patient medical parameter data and for synchronization of processing of medical parameter data concurrently acquired from a single particular patient. The master clock generator is programmed by dividing a clock signal to provide a desired clock frequency in response to received frequency selection command data. An output interface provides synchronization clocks to the multiple different medical devices for acquiring patient medical parameter data and providing synchronized output patient medical parameter data from the different medical devices for presentation to a user in synchronized format on a display. An input interface receives the command data for determining clock division and generating the desired clock frequency.

16 Claims, 3 Drawing Sheets

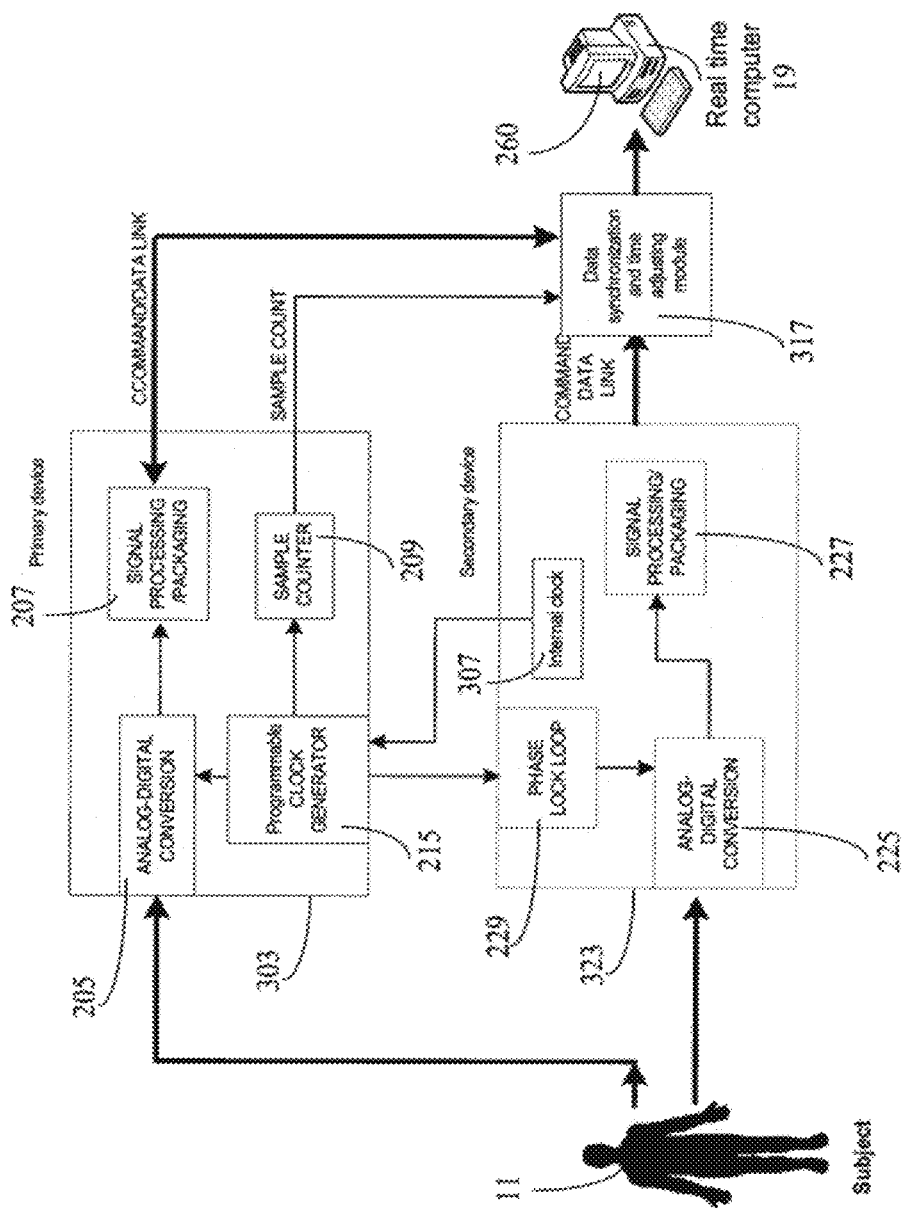

MEDICAL DEVICE SYNCHRONIZATION SYSTEM FOR USE IN CARDIAC AND OTHER PATIENT MONITORING

This is a non-provisional application of provisional application Ser. No. 60/989,220 filed Nov. 20, 2007, by H. Zhang et al.

FIELD OF THE INVENTION

This invention concerns a system for synchronizing multiple different patient medical parameter processing devices using adaptively programmable synchronization clocks to provide synchronized output patient medical parameter data from the different medical devices for presentation to a user in synchronized format on a display.

BACKGROUND OF THE INVENTION

Medical patient monitoring and procedure devices within a Cardiology Laboratory, for example, are typically unable to mutually synchronize data and the devices acquire and process signal data at different sampling rates. For instance, Internal Cardiac Signals and Surface Lead EKG Signals, because of their high frequency components, require sampling rates of 1000 Hz or more whereas respiration signals only require sampling rates of 100 Hz or less as the frequency components of respiration signals are much lower. Invasive Blood Pressure signals employ sampling rates of 200 Hz. The lack of synchronization of medical devices processing these different acquired medical signals reduces reliability and impairs diagnosis of data during cardiac catheter procedures, for example.

In addition, cardiac procedures treat cardiac events with RF energy (ablation), involving burning of cardiac tissue to reroute a conductive path of the heart, for example. In many cardiac events such as Atrial Fibrillation, a user ablates cardiac tissue to normalize patient heart rhythm and synchronizing acquisition and processing of patient parameter signal data with an ablation instrument improves treatment of Atrial Fibrillation, for example. Delay in ablation therapy occurs when the time it takes to realize a cardiac event such as an atrial fibrillation is occurring is too long and the cardiac event goes into remission before ablation therapy can be performed. Further, ablation therapy delay is exacerbated by sampling rate differences between multiple measurement devices, latency within each measurement device and bus issues arising from the use of a single bus linking the medical devices. Also, risk of misdiagnosis based on mis-aligned or mis-synchronized waveforms and signals provided by multiple acquisition devices is increased due to time delay between output of different patient parameter signal data processing devices for presentation in a display and different data sampling rates. A system according to invention principles addresses these deficiencies and related problems.

SUMMARY OF THE INVENTION

A system provides synchronization between different medical signal (e.g., EKG and ICEG signal) acquisition and processing devices to ensure signals are in phase with each other to prevent misdiagnosis in real time diagnosis and provide synchronized medical parameter presentation to a user in a display. A system synchronizes multiple different patient medical parameter processing devices, using a master clock generator. The master clock generator is adaptively programmable to provide synchronization clocks having frequencies compatible with multiple different medical devices for acquiring patient medical parameter data and for synchronization of processing of medical parameter data concurrently acquired from a single particular patient. The master clock generator is programmed by dividing a clock signal to provide a desired clock frequency in response to received frequency selection command data. An output interface provides synchronization clocks to the multiple different medical devices for acquiring patient medical parameter data and providing synchronized output patient medical parameter data from the different medical devices for presentation to a user in synchronized format on a display. An input interface receives the command data for determining clock division and generating the desired clock frequency.

BRIEF DESCRIPTION OF THE DRAWING

FIG. 3 shows a system for synchronizing multiple different patient medical parameter processing devices and supporting bidirectional communication between a master and subordinate medical devices, according to invention principles.

DETAILED DESCRIPTION OF THE INVENTION

Figure 1:
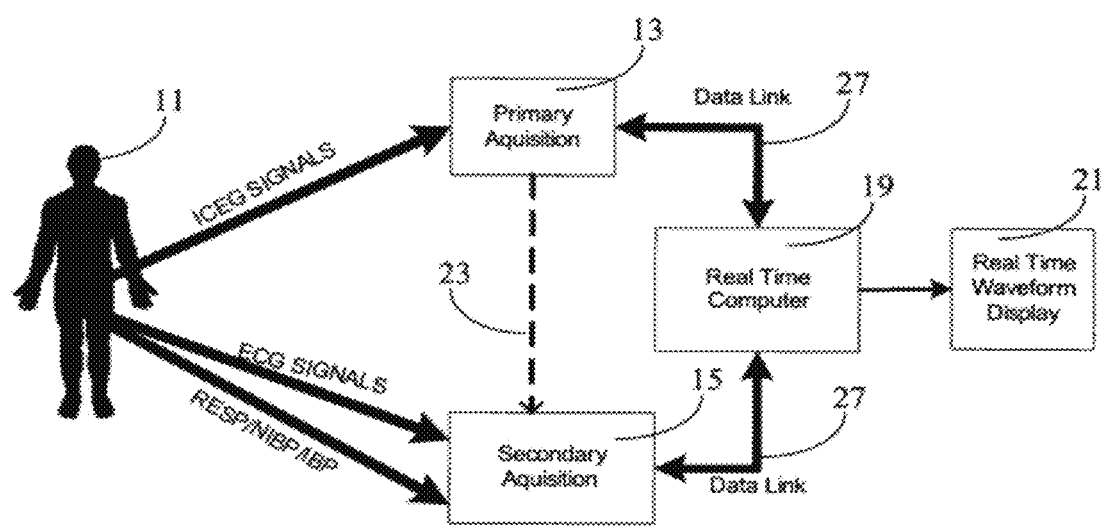
FIG. 1 shows an overview of a patient medical parameter acquisition configuration, according to invention principles.

In a typical catheter laboratory environment it is common for two or more vital-sign data-acquisition units to be used having different sampling rates and that are not mutually synchronized, resulting in output waveforms being out of phase. The inventors have advantageously recognized that synchronization between different medical signal (e.g., ECG electro-cardiogram and ICEG intracardiac electrogram) acquisition and processing devices is desirable to improve real time diagnosis, cost effectiveness and minimize signal delay effects. A system synchronizes data processing of different medical signal acquisition and processing devices and ensures signals are in phase with each other to prevent misdiagnosis in real time diagnosis and provide synchronized medical parameter presentation to a user in a display. In operation, devices such as an EKG acquisition unit and an ICEG acquisition unit measure the same electrical potential of the heart.

The system ensures that signals from an EKG and an ICEG unit are in phase with each other to prevent misdiagnosis. In one embodiment, the system provides a master unit that generates a clock and distributes the clock to slave acquisition units so the different systems synchronize medical parameter acquisition. A clock counter in the master unit tracks the number of clocks sent by the master unit to secondary acquisition units. In a second embodiment, acquired patient medical parameter data from secondary medical devices is communicated in digital signals to a centralized master unit comprising a real time computer or a microprocessor in conjunction with a display. The master unit processes and conditions digital data and waveforms and performs data analysis and presents processed data to a user in synchronized format on a display.

The system addresses sampling rate differences between multiple medical signal acquisition and processing devices and time delay in device processing and output of different patient parameter signal data for presentation in a display. The system addresses time discrepancies between different patient parameter acquisition devices resulting from sampling data at different rates and reduces time delay between the devices (e.g., to within 1 ms) and synchronizes waveforms of the same nature (e.g., ICEG and ECG signals). The system minimizes latency occurring due to signal delay within individual patient parameter acquisition devices. The system also synchronizes data using clocks provided by a master device to secondary devices and using individually programmable delays for data provided by individual devices. This addresses the problems that arise due to different signal delays between devices. The system employs signal analysis to detect atrial fibrillation and communicates a trigger to a medical device such as an ablator to improve efficiency in a cardiac laboratory. This system reduces need for human intervention to detect an atrial fibrillation and perform necessary ablation.

A processor as used herein is a device for executing stored machine-readable instructions for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. Workflow comprises a sequence of tasks performed by a device or worker or both. An object or data object comprises a grouping of data, executable instructions or a combination of both or an executable procedure.

FIG. 1 shows an overview of a patient medical parameter (vital sign) acquisition configuration. Primary Medical Signal Acquisition Device 13 acquires ICEG data and one or more Secondary Medical Signal Acquisition Devices e.g., device 15 that acquires ECG data and respiratory and blood pressure data from patient 11. Devices 13 and 15, in the absence of synchronization, acquire and process unsynchronized, biometric data sets from patient 11. The system synchronizes devices 13 and 15 using a clock signal 23 provided by device 13 to device 15 to synchronize different acquisition units so the devices are able to sample data at the same time. Further, output data from devices 13 and 15 is provided to real-time computer 19 that delays output data from one or more devices 13 and 15 to ensure data is synchronized for presentation and comparison in a composite display image as real time waveform display 21, for example. The ICEG data acquired by device 13 needs to be sampled at a higher frequency than Respiration or ECG data acquired by device 15. Typical ICEG or ECG acquisition units can sample data anywhere from 250 Hz to 4 KHz, while respiration devices will acquire data in the 100 Hz range. Therefore the system synchronizes Primary Acquisition device 13 operating at the highest system sampling rate with lower sampling rate device 15.

Clock signal 23 triggers sampling by acquisition device 15 that employ the same or lower sampling rates. A synchronization clock may be 20 KHz, for example, so that downstream acquisition units divide the clock into lower frequencies to meet individual device sampling rate requirements. Data Link 27 conveys commands from real time computer 19 to computers in acquisition devices 13 and 15 that adjust for signal latency between the multiple medical devices as well as provide a means for centralized computer 19 to acquire data from different medical devices 13 and 15 for display as waveforms 21. Data link 27 comprises an Ethernet connection, for example.

Figure 2:
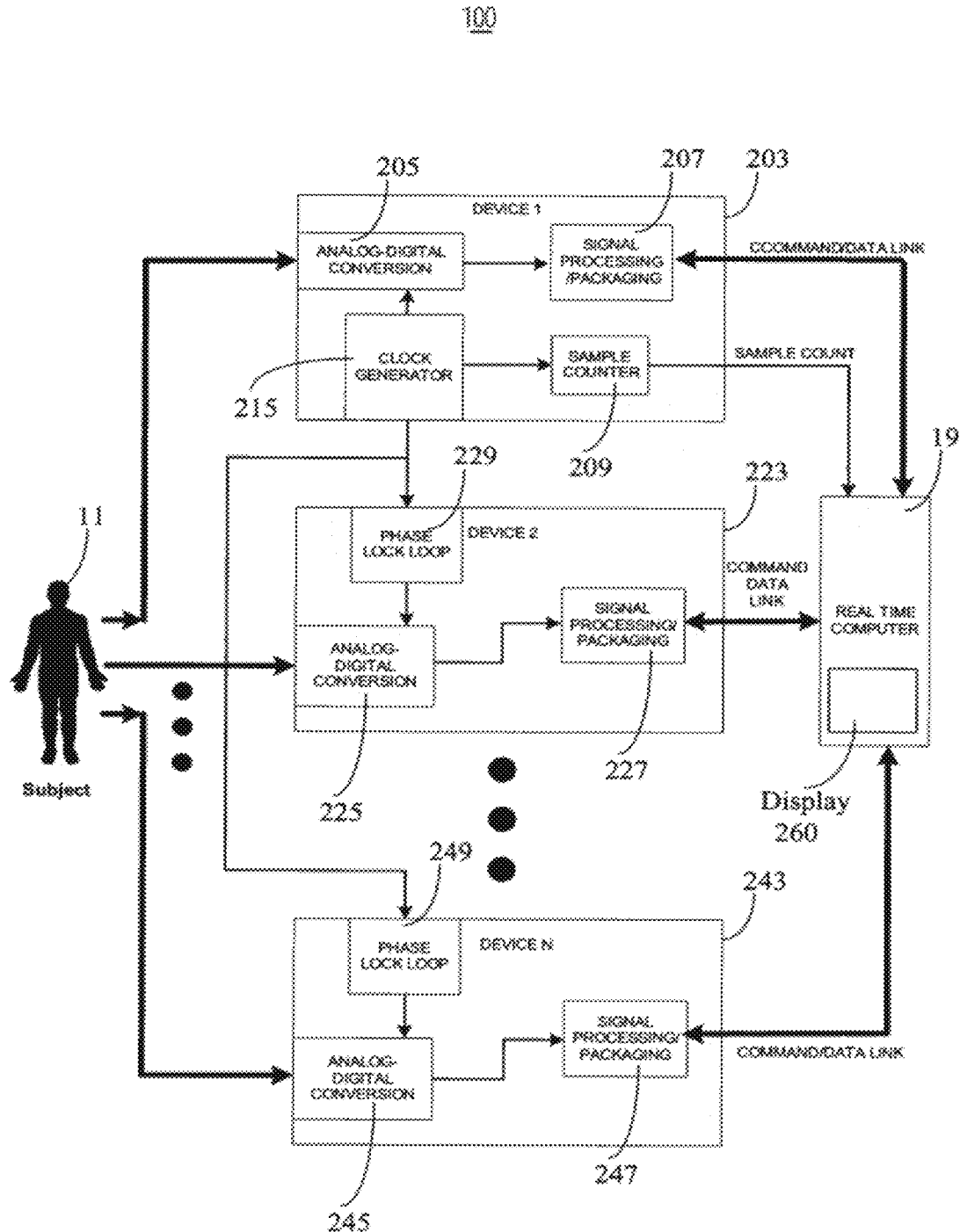
FIG. 2 shows a system for synchronizing multiple different patient medical parameter processing devices, according to invention principles.

FIG. 2 shows system 100 for synchronizing multiple different patient medical parameter processing devices 203, 223 and 243 that measure and synchronize different biometric parameters using a common clock from master device 203 that employs the highest system data sampling rate. The patient medical parameter data comprises one or more of, (a) ECG and ICEG data, (b) a blood oxygen representative parameter, (c) a change in a blood oxygen representative parameter, (d) a rate of change of a blood oxygen representative parameter, (e) a patient temperature, (f) a arterial blood pressure, (g) a hematocrit level, (h) a cardiac index (i) a pulse rate and (j) a change in pulse rate. Processing devices 203, 223 and 243 respectively include analog to digital converters 205, 225 and 245 as well as signal processing units 207, 227 and 247.

Analog to digital converters 205, 225 and 245 in conjunction with respective signal processing units 207, 227 and 247 process vital sign signals acquired from patient 11 and provide processed output signals to real-time computer 19. In one embodiment, primary medical parameter processing device 203 generates a clock frequency that is higher (or the same as) that employed by secondary processing devices 223 and 243 and has a sampling rate that is higher (or the same as) that employed by secondary processing devices 223 and 243. Master clock generator 215 in unit 203 is adaptively programmable to provide synchronization clocks having frequencies compatible with different secondary processing devices 223 and 243 and any associated trigger signals. The synchronization clocks and trigger signals enable synchronization of processing of medical parameter data concurrently acquired by different secondary processing devices 223 and 243 from single particular patient 11. Master clock generator 215 is programmed by dividing a clock signal to provide a desired clock frequency in response to received frequency selection command data.

Master clock generator 215 typically generates acquisition clocks at lower frequencies but in phase with a primary clock, ensuring signals being acquired are mutually in phase. Master clock generator 215 also adaptively adjusts pulse width in response to received frequency selection command data. Phase lock loop circuitry in synchronization interface 229 and 249 produce clocks at lower frequencies to acquire data at lower sampling rates. Generated in-phase clock signals are distributed to analog to digital converters 225 and 245 so they can acquire data in phase with the master clock. Unit 203 includes an output interface for providing the synchronization clocks to different secondary processing devices 223 and 243 and for providing synchronized output patient medical parameter data from signal processing unit 207 to computer 19 for analysis, processing and presentation to a user in synchronized format on a display 260. Unit 203 also includes an input interface for receiving the command data for determining clock division and generating the desired clock frequency.

Different secondary processing devices 223 and 243 individually have synchronization interfaces 229 and 249 for receiving and using a synchronization clock provided by master clock generator 215 for synchronizing processing of patient medical parameter data acquired concurrently from single particular patient 11. Synchronization interfaces 229 and 249 include phase lock loop circuitry that locks on a clock signal from master clock generator 215 and generates acquisition clocks for its own device sampling rate requirements. Lower frequency clocks are generated within the phase lock loop circuitry so that respective analog to digital converters 205, 225 and 245 sample data in phase with processing devices 203. Synchronization interfaces 229 and 249 enable different secondary processing devices 223 and 243 to provide synchronized output patient medical parameter data to computer 19 for presentation to a user in synchronized format on display 260.

In one embodiment, an auto-discovery communication interface in clock generator 215 automatically communicates with different medical devices 223 and 243 to determine a frequency (and sampling rate requirements) and provide the frequency selection command data. For example, if primary device 203 determines the internal clock (speed) of secondary medical devices 223 and 243, primary device unit 215 can adjust, control and provide time clocks to these devices for synchronization of the devices. Master clock generator 215 may reside in computer 19, one or more devices 203, 223 and 243 or elsewhere on a network (e.g., an Ethernet network) linking the FIG. 2 elements. In another embodiment, a user interface in computer 19 generates data representing at least one display image enabling a user to enter data comprising the frequency selection command data.

Real-time computer 19 includes an adaptive delay generator for adaptively generating a time delay used in delaying synchronized output patient medical parameter data from one of medical parameter processing devices 203, 223 and 243 for presentation on display 260 to a user synchronized with output patient medical parameter data from the remaining medical parameter processing devices 203, 223 and 243 in response to received time delay selection command data. Clock counter 209 in master device 203 tracks the number of clocks sent by master device 203 to secondary devices 223 and 243 and provides a count value to real-time computer 19. The count value is provided for each clock or for a periodic count multiple, for example. The sample counter value is used by real time computer 19 to delay and synchronize samples that are received from secondary medical devices 223 and 243 with the samples received from primary medical device 203. In one embodiment, the adaptive delay generator may be located in one or more of medical parameter processing devices 203, 223 and 243. Further, individual devices 203, 223 and 243 send synchronized output patient medical parameter data to Real Time Computer 19 for further signal processing and display. In another embodiment, the adaptive delay generator may be located on a network linking the FIG. 2 elements.

FIG. 3 shows system 200 for synchronizing multiple different patient medical parameter processing devices and supporting bidirectional communication between master device 303 and subordinate medical device 323 using automated programmable clock generation in synchronizing the data between primary and secondary medical devices. System 200 is similar to the previously described system 100 (FIG. 2). Master device 303 (corresponding to FIG. 2 device 203) unit 215 includes an auto-discovery communication interface for automatically communicating with different medical devices, such as device 323, to determine a clock frequency and provide the clock frequency selection command data. Unit 215 derives a time clock for a secondary device, by monitoring and adjusting a suitable clock (synchronized with a primary clock) to provide a clock for a secondary device. The data in system 200 is also trackable by time stamp provided by unit 209. Interface 307 provides data to device 303 indicating an internal clock frequency required for synchronization of device 323 with device 303.

In addition, data synchronization and time delay adjusting unit 317 automatically adjusts delay of output patient medical parameter data from different medical devices 303 and 323 for presentation to a user in synchronized format on a display 260 via computer 19. Unit 317 may reside in computer 19, one or more devices 303 and 323 or elsewhere on a network (e.g., an Ethernet network) linking the FIG. 3 elements. Unit 317 comprises an adaptive delay generator for adaptively generating a time delay used in delaying synchronized output patient medical parameter data from medical device 323 for presentation to a user synchronized with output patient medical parameter data from medical device 303 for presentation on display 260 in response to received time delay selection command data. The time delay has a value independently adjustable of the desired clock frequency. The adaptive delay generator adaptively generates first and second different time delays used in delaying synchronized output patient medical parameter data from medical devices 303 and 323 for presentation to a user in synchronized format on display 260 in response to received time delay selection command data.

A user interface in computer 19 generates data representing at least one display image enabling a user to enter data comprising the time delay selection command data. In one embodiment, unit 317 includes an auto-discovery communication interface for automatically communicating with medical devices 303 and 323 to determine a time delay and provide the time delay selection command data. Time delay of output patient medical parameter data to be corrected is monitored by Real-Time computer 19. Control signals sent from real-time computer 19 in conjunction with unit 317, to primary and secondary medical devices 303 and 323, provide an accurate signal delay adjustment value (e.g., based on sample counts provided by unit 209) to correct for time delay of output patient medical parameter data. The adjustment value is used by unit 317 (or in another embodiment medical device 303 and 323 to adjust output patient medical parameter data delay. The adjustment value may be delivered to an FPGA in unit 317 or to a data packing and stream generator in one or more of medical devices 303 and 323, for example and used to either speed up or slow down patient medical parameter data processing.

System 200 reduces misdiagnosis of cardiac events due to lack of synchronization between multiple medical devices, latency of signals between different medical devices and delay in tissue ablation therapy, for example. Misdiagnosis may occur if signals being acquired by different medical devices are out of phase. For instance, if a QRS complex of a surface EKG waveform is not in-line with the QRS complex of an internal EKG waveform, a user is not able to distinguish if a patient has a problem and may treat a problem that may not exist or fail to treat a problem that does exist. Signal latency occurs when a signal path within one medical parameter data acquisition device is not equal to a signal path of another medical parameter data acquisition device. For instance, the time it takes an EKG signal to be acquired, digitally converted, processed, packaged and sent over a data link to real time computer 19 may be different than the time it takes for an ICEG signal to undergo a corresponding process in a different device. This mis-match results from inherent time differences between different semiconductor devices that process the medical parameter data, for example. Further, delay in tissue ablation therapy occurs if there is delay in the time it takes to realize a cardiac event such as atrial fibrillation is occurring and the cardiac event goes into remission before ablation therapy is performed. In one embodiment, a unit automatically detects atrial fibrillation and triggers an ablator to ensure patient treatment is delivered on time.

In a further embodiment, a synchronization clock signal provided by master clock generator 215 is replaced with acquired medical parameter data. Medical parameter data acquired by a medical data acquisition device with the highest sampling rate is communicated in a digital stream to medical data acquisition devices with lower sampling rates. The digital stream is analyzed by devices downstream and synchronized with the data being acquired, processed, packaged and sent to a centralized location for further processing and display.

System 200 (FIG. 3) provides reliable data synchronization for one dimensional signals such as 12 lead ECG and intra-cardiac electrogram signals and multi-dimensional data. For example, during patient monitoring, a one dimensional signal (e.g., a surface ECG signal) is used for gating, synchronizing and triggering an image acquisition system, such as a 2D or 3D X-ray or ultrasound imaging. System 200 also synchronizes acquired patient signals with derived patient data and signals, such as QRS trigger signals (derived from 12 lead ECG signals) to trigger image hardware scanning and acquisition, for example. System 200 provides acquired patient signal data and command synchronization to eliminate or reduce time delay between different medical devices to accommodate differences in both, sampling time clock and transmission rate between medical data acquisition devices. System 200 in addition advantageously accommodates differences in time delay of processed output medical parameter data between medical data acquisition devices.

The systems and processes of FIGS. 1-3 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system links multiple different medical devices for acquiring patient medical parameter data that individually have a synchronization interface for receiving and using a synchronization clock provided by a master clock generator for synchronizing processing of patient medical parameter data acquired concurrently from a single particular patient. This enables the multiple different medical devices to provide synchronized output patient medical parameter data for presentation to a user in synchronized format on a display. The processes and applications may, in alternative embodiments, be located on one or more (e.g., distributed) processing devices accessing a network linking the elements of FIGS. 2 and 3. Further, any of the functions and steps provided in FIGS. 1-3 may be implemented in hardware, software or a combination of both and may reside on one or more processing devices located at any location of a network linking the elements of FIGS. 2-3 or another linked network, including the Internet.

What is claimed is:

1. A system for synchronizing a plurality of different patient medical parameter processing devices, comprising:
   a master clock generator adaptively programmable to provide synchronization clocks having frequencies compatible with a plurality of different medical devices for synchronization of processing of medical parameter data concurrently acquired from a single particular patient, said master clock generator being programmed by dividing a clock signal to provide a desired clock frequency in response to received frequency selection command data, said plurality of different medical devices being for acquiring patient medical parameter data;
   an adaptive delay generator for adaptively generating a time delay used in delaying synchronized output patient medical parameter data from one of said different medical devices for presentation to a user synchronized with output patient medical parameter data from another of said different medical devices for presentation on a display in response to received time delay selection command data;
   an output interface for providing said synchronization clocks to said plurality of different medical devices; and
   an input interface for receiving said frequency selection command data for determining clock division.

2. A system according to claim 1, including
   a plurality of different medical devices for acquiring patient medical parameter data, said plurality of different medical devices individually having a synchronization interface for receiving and using a synchronization clock provided by said master clock generator for synchronizing processing of patient medical parameter data acquired concurrently from said single particular patient enabling said plurality of different medical devices to provide synchronized output patient medical parameter data for presentation to a user in synchronized format on a display.

3. A system according to claim 2, wherein
   said synchronization interface comprises a phase lock loop.

4. A system according to claim 1, wherein
said adaptive delay generator adaptively generates said time delay to reduce latency occurring due to signal delay within individual different medical devices using individually programmable delays for data provided by individual devices.

5. A system according to claim 1, wherein
said adaptive delay generator adaptively generates first and second different time delays used in delaying synchronized output patient medical parameter data from first and second different medical devices for presentation to a user in synchronized format on said display in response to received time delay selection command data.

6. A system according to claim 1, wherein
said time delay has a value independently adjustable of said desired clock frequency.

7. A system according to claim 1, including
a user interface for generating data representing at least one display image enabling a user to enter data comprising said time delay selection command data.

8. A system according to claim 1, including
an auto-discovery communication interface for automatically communicating with said different medical devices to determine a time delay and provide said time delay selection command data.

9. A system according to claim 1, including
a user interface for generating data representing at least one display image enabling a user to enter data comprising said frequency selection command data.

10. A system according to claim 1, including
an auto-discovery communication interface for automatically communicating with said different medical devices to determine a frequency and provide said frequency selection command data.

11. A system according to claim 1, wherein
said patient medical parameter data comprises at least two of, (a) ECG data, (b) a blood oxygen representative parameter, (c) a change in a blood oxygen representative parameter, (d) a rate of change of a blood oxygen representative parameter, (e) a patient temperature, (f) a arterial blood pressure, (g) a hematocrit level, (h) a cardiac index (i) a pulse rate and (j) a change in pulse rate.

12. A system according to claim 1, wherein
said master clock generator adaptively adjusts pulse width in response to received frequency selection command data.

13. A system according to claim 1, wherein
said master clock generator is included in one of said different medical devices.

14. A system used by a patient medical parameter processing device in synchronizing patient medical parameter processing of a plurality of medical parameter processing devices, comprising:
an input interface for receiving a synchronization clock provided by a master clock generator and a time delay generated by an adaptive delay generator;
a synchronization interface for using said synchronization clock for synchronizing processing of patient medical parameter data acquired concurrently from a single particular patient enabling a plurality of different medical devices to provide synchronized output patient medical parameter data and delaying said synchronized output patient medical parameter data from one of said different medical devices for presentation to a user synchronized with output patient medical parameter data from another of said different medical devices for presentation on a display in response to the received time delay, the delayed synchronized output patient medical parameter data being for presentation to a user in synchronized format on a display; and
an output interface for providing said delayed synchronized output patient medical parameter data for synchronized display with output patient medical parameter data provided by another of said plurality of different medical devices for presentation to a user in synchronized format on a display.

15. A system according to claim 14, including
a master clock generator adaptively programmable to provide synchronization clocks having frequencies compatible with a plurality of different medical devices for synchronization of processing of medical parameter data concurrently acquired from a single particular patient, said master clock generator being programmed by dividing a clock signal to provide a desired clock frequency in response to received frequency selection command data.

16. A system for synchronizing a plurality of different patient medical parameter processing devices, comprising:
a master clock generator adaptively programmable to provide synchronization clocks having frequencies compatible with a plurality of different medical devices for synchronization of processing of medical parameter data concurrently acquired from a single particular patient, said master clock generator being programmed by dividing a clock signal to provide a desired clock frequency in response to received frequency selection command data;
an output interface for providing said synchronization clocks to a plurality of different medical devices for use by said plurality of different medical devices in acquiring patient medical parameter data using a synchronization clock provided by said master clock generator for synchronizing processing of patient medical parameter data acquired concurrently from said single particular patient enabling said plurality of different medical devices to provide synchronized output patient medical parameter data for presentation to a user in synchronized format on a display;
an input interface for receiving said frequency selection command data for determining clock division; and
an adaptive delay generator for adaptively generating a time delay used in delaying synchronized output patient medical parameter data from one of said different medical devices for presentation to a user synchronized with output patient medical parameter data from another of said different medical devices for presentation on said display in response to received time delay selection command data.

* * * * *